United States Patent
Voisard et al.

(10) Patent No.: US 9,357,996 B2
(45) Date of Patent: *Jun. 7, 2016

(54) FIXATION DEVICE WITH MAGNESIUM CORE

(71) Applicant: DePuy Synthes Products, Inc., Raynham, MA (US)

(72) Inventors: Cyril Voisard, Maegenwil (CH); Nicolas Bouduban, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,054

(22) Filed: Mar. 26, 2015

(65) Prior Publication Data

US 2015/0196291 A1    Jul. 16, 2015

Related U.S. Application Data

(63) Continuation of application No. 13/222,867, filed on Aug. 31, 2011, now Pat. No. 9,023,088.

(60) Provisional application No. 61/380,884, filed on Sep. 8, 2010.

(51) Int. Cl.
*A61B 17/84* (2006.01)
*A61B 17/68* (2006.01)
(Continued)

(52) U.S. Cl.
CPC ......... *A61B 17/0401* (2013.01); *A61B 17/0642* (2013.01); *A61B 17/68* (2013.01); *A61B 17/866* (2013.01); *A61L 31/022* (2013.01); *A61L 31/10* (2013.01); *A61L 31/14* (2013.01);
(Continued)

(58) Field of Classification Search
CPC .. A61B 17/72; A61B 17/7233; A61B 17/725; A61B 17/7258; A61B 17/7275; A61B 17/7283; A61B 17/7291; A61B 17/84; A61B 17/86; A61B 17/8625; A61B 17/8645; A61B 17/866; A61B 2017/8655
USPC .................. 606/232, 300–321, 326–328, 331
See application file for complete search history.

(56) References Cited

U.S. PATENT DOCUMENTS 4,385,136 A * 5/1983 Ancker et al. ................ 523/215
RE31,992 E * 9/1985 Ancker et al. ................ 523/202
(Continued)

FOREIGN PATENT DOCUMENTS

EP    1506790    2/2005
EP    1611852    1/2006
(Continued)

OTHER PUBLICATIONS

Zberg. Biocompatible Mg-based glasses: towards a new class of degradable implants, n. d. Web Nov 8, 2013. <http://e-collection.library.ethz.ch/eserv/eth :928/eth-928-01 .pdf>.*

*Primary Examiner* — Christian Sevilla
*Assistant Examiner* — Eric S Gibson
(74) *Attorney, Agent, or Firm* — Baker & Hostetler LLP

(57) ABSTRACT

A fixation device comprises a biodegradable inner core extending along a longitudinal axis from a distal tip to a proximal end in combination with a sleeve surrounding the core along a portion of a length thereof and comprising a thermoplastic polymer formed of a material which softens and expands into surrounding bone tissue when activated by an energy source.

19 Claims, 3 Drawing Sheets

(51) Int. Cl.
*A61B 17/04* (2006.01)
*A61B 17/064* (2006.01)
*A61B 17/86* (2006.01)
*A61L 31/02* (2006.01)
*A61L 31/10* (2006.01)
*A61L 31/14* (2006.01)
*A61B 17/00* (2006.01)

(52) U.S. Cl.
CPC .... *A61L 31/148* (2013.01); *A61B 2017/00004* (2013.01); *A61B 2017/00411* (2013.01); *A61B 2017/042* (2013.01); *A61B 2017/0403* (2013.01); *A61B 2017/0414* (2013.01); *A61B 2017/0448* (2013.01)

(56) References Cited

U.S. PATENT DOCUMENTS

| | | | | |
|---|---|---|---|---|
| 5,496,289 | A * | 3/1996 | Wenstrom, Jr. | 604/264 |
| 5,720,765 | A * | 2/1998 | Thal | 606/232 |
| 5,728,136 | A * | 3/1998 | Thal | 606/232 |
| 5,792,142 | A * | 8/1998 | Galitzer | 606/65 |
| 5,849,004 | A * | 12/1998 | Bramlet | 606/232 |
| 5,993,477 | A * | 11/1999 | Vaitekunas et al. | 606/232 |
| 6,132,214 | A * | 10/2000 | Suhonen et al. | 433/201.1 |
| 6,139,565 | A * | 10/2000 | Stone et al. | 606/232 |
| 6,368,326 | B1 * | 4/2002 | Dakin et al. | 606/103 |
| RE37,963 | E * | 1/2003 | Thal | 606/232 |
| 6,517,542 | B1 * | 2/2003 | Papay et al. | 606/232 |
| 6,913,666 | B1 * | 7/2005 | Aeschlimann et al. | 156/73.1 |
| 6,921,264 | B2 * | 7/2005 | Mayer et al. | 433/173 |
| 6,981,974 | B2 * | 1/2006 | Berger | 606/304 |
| 6,984,241 | B2 * | 1/2006 | Lubbers et al. | 606/232 |
| 7,008,226 | B2 * | 3/2006 | Mayer et al. | 433/173 |
| 7,090,690 | B2 * | 8/2006 | Foerster et al. | 606/232 |
| 7,189,251 | B2 * | 3/2007 | Kay | 606/232 |
| 7,491,217 | B1 * | 2/2009 | Hendren et al. | 606/232 |
| 7,678,138 | B2 * | 3/2010 | Fitts et al. | 606/300 |
| 7,708,767 | B2 * | 5/2010 | Contiliano et al. | 606/301 |
| 7,785,347 | B2 * | 8/2010 | Harvie et al. | 606/232 |
| 7,942,986 | B2 * | 5/2011 | Bettles et al. | 148/420 |
| 8,089,029 | B2 * | 1/2012 | Flanagan | 219/121.7 |
| 8,221,119 | B1 * | 7/2012 | Valen | 433/174 |
| 8,268,235 | B2 * | 9/2012 | Gerold | 420/406 |
| 8,298,262 | B2 * | 10/2012 | Stone et al. | 606/232 |
| 8,313,692 | B2 * | 11/2012 | Somekawa et al. | 420/408 |
| 8,475,608 | B2 * | 7/2013 | Osawa et al. | 148/420 |
| 8,551,140 | B2 * | 10/2013 | Denham et al. | 606/232 |
| 8,574,275 | B2 * | 11/2013 | Stone et al. | 606/313 |
| 8,834,542 | B2 * | 9/2014 | Mayer et al. | 606/310 |
| 2002/0049447 | A1 * | 4/2002 | Li | 606/73 |
| 2002/0095064 | A1 * | 7/2002 | Beyar | 600/30 |
| 2003/0039676 | A1 | 2/2003 | Boyce et al. | |
| 2003/0111142 | A1 * | 6/2003 | Horton et al. | 148/561 |
| 2003/0216780 | A1 * | 11/2003 | Fitts et al. | 606/232 |
| 2004/0010273 | A1 * | 1/2004 | Diduch et al. | 606/144 |
| 2005/0079088 | A1 * | 4/2005 | Wirth et al. | 420/402 |
| 2006/0271105 | A1 * | 11/2006 | Foerster et al. | 606/232 |
| 2007/0005069 | A1 * | 1/2007 | Contiliano et al. | 606/73 |
| 2007/0198017 | A1 * | 8/2007 | Tschakaloff et al. | 606/73 |
| 2007/0207186 | A1 * | 9/2007 | Scanlon et al. | 424/424 |
| 2007/0260259 | A1 * | 11/2007 | Fanton et al. | 606/99 |
| 2008/0021474 | A1 * | 1/2008 | Bonutti et al. | 606/64 |
| 2008/0045962 | A1 * | 2/2008 | Aeschlimann et al. | 606/72 |
| 2008/0103594 | A1 * | 5/2008 | Loffler et al. | 623/11.11 |
| 2008/0109038 | A1 * | 5/2008 | Steiner et al. | 606/232 |
| 2008/0125815 | A1 * | 5/2008 | Heaven et al. | 606/308 |
| 2008/0175744 | A1 * | 7/2008 | Motegi et al. | 420/409 |
| 2008/0215098 | A1 * | 9/2008 | Imwinkelried et al. | 606/301 |
| 2008/0234682 | A1 * | 9/2008 | Park | 606/75 |
| 2008/0234730 | A1 * | 9/2008 | Cotton et al. | 606/232 |
| 2008/0275469 | A1 * | 11/2008 | Fanton et al. | 606/139 |
| 2009/0062854 | A1 * | 3/2009 | Kaiser et al. | 606/232 |
| 2009/0131938 | A1 * | 5/2009 | Khatri et al. | 606/70 |
| 2009/0131980 | A1 * | 5/2009 | Wiesman et al. | 606/228 |
| 2009/0198320 | A1 * | 8/2009 | Mueller et al. | 623/1.38 |
| 2009/0208428 | A1 * | 8/2009 | Hill et al. | 424/52 |
| 2009/0228104 | A1 * | 9/2009 | Strzepa et al. | 623/14.12 |
| 2009/0246070 | A1 * | 10/2009 | Tokuda et al. | 420/407 |
| 2009/0292321 | A1 * | 11/2009 | Collette | 606/303 |
| 2009/0312793 | A1 * | 12/2009 | Huxel et al. | 606/232 |
| 2010/0023057 | A1 * | 1/2010 | Aeschlimann et al. | 606/246 |
| 2010/0036441 | A1 * | 2/2010 | Procter | 606/329 |
| 2010/0063211 | A1 * | 3/2010 | Kaszas et al. | 525/98 |
| 2010/0131052 | A1 * | 5/2010 | Kappelt et al. | 623/1.46 |
| 2010/0145393 | A1 * | 6/2010 | Fallin et al. | 606/301 |
| 2010/0145432 | A1 * | 6/2010 | Bayer et al. | 623/1.15 |
| 2010/0168841 | A1 * | 7/2010 | Furst et al. | 623/1.42 |
| 2010/0198332 | A1 * | 8/2010 | Gerold | 623/1.15 |
| 2010/0210745 | A1 * | 8/2010 | McDaniel et al. | 521/55 |
| 2010/0234950 | A1 * | 9/2010 | Tsutsumi et al. | 623/16.11 |
| 2010/0241229 | A1 * | 9/2010 | Baehre et al. | 623/16.11 |
| 2010/0249832 | A1 * | 9/2010 | Stopek et al. | 606/232 |
| 2010/0249838 | A1 * | 9/2010 | Stopek et al. | 606/246 |
| 2010/0249854 | A1 * | 9/2010 | Thomas et al. | 606/301 |
| 2010/0249944 | A1 * | 9/2010 | Thomas et al. | 623/23.57 |
| 2010/0267884 | A1 * | 10/2010 | Kaszas et al. | 524/500 |
| 2010/0331896 | A1 * | 12/2010 | Le Couedic et al. | 606/305 |
| 2011/0015684 | A1 * | 1/2011 | Belcheva et al. | 606/314 |
| 2011/0046682 | A1 * | 2/2011 | Stephan et al. | 606/305 |
| 2011/0076178 | A1 * | 3/2011 | Somekawa et al. | 420/408 |
| 2011/0238149 | A1 * | 9/2011 | Atanasoska et al. | 623/1.15 |
| 2011/0240064 | A1 * | 10/2011 | Wales et al. | 134/26 |
| 2011/0250626 | A1 * | 10/2011 | Williams et al. | 435/18 |
| 2011/0301281 | A1 * | 12/2011 | Kaszas et al. | 524/525 |
| 2011/0313527 | A1 * | 12/2011 | Witte et al. | 623/11.11 |
| 2011/0319986 | A1 * | 12/2011 | Bayer et al. | 623/1.46 |
| 2012/0059429 | A1 * | 3/2012 | Voisard et al. | 606/313 |
| 2012/0097194 | A1 * | 4/2012 | McDaniel et al. | 134/26 |
| 2012/0143227 | A1 * | 6/2012 | Steckel et al. | 606/151 |

FOREIGN PATENT DOCUMENTS

| | | |
|---|---|---|
| JP | 2001-503298 | 3/2001 |
| JP | 2001-517999 | 10/2001 |
| WO | WO 98/19606 | 5/1998 |
| WO | WO 99/37216 | 7/1999 |
| WO | WO 2009/109057 | 9/2009 |
| WO | WO 2010/045749 | 4/2010 |

* cited by examiner

FIXATION DEVICE WITH MAGNESIUM CORE

PRIORITY CLAIM

The present application is a continuation application of U.S. patent application Ser. No. 13/222,867 filed on Aug. 31, 2011 and entitled "Fixation Device with Magnesium Core" which, in turn, claims priority to U.S. Provisional Application Ser. No. 61/380,884 filed on Sep. 8, 2010 and entitled "Fixation Device with Magnesium Core," the entire disclosure of which is incorporated herein by reference.

FIELD OF THE INVENTION

The present invention generally relates to fixation devices for use in suturing of soft tissue to bone and in bone fixation. More particularly, the present invention relates to a fixation device comprising a core of a biodegradable metal or metal alloy. An exemplary embodiment of the invention relates to a method for inserting the fixation device.

BACKGROUND

Soft tissue tears, bone fracture or joint dislocation all generally require a fixation device to be correctly treated. In some cases, however, drilling a hole to accommodate the fixation device and/or tapping the fixation device into the bone may damage or split the bone. These damaged bones may be repaired by inserting, for example, a revision implant therethrough. For some small and/or thin bones, however, insertion of a revision implant may be difficult or even impossible.

SUMMARY OF THE INVENTION

The present invention relates to a bone anchor having a longitudinal axis, an inner core including a tip coaxial with the longitudinal axis and a sleeve surrounding the core and comprising a thermoplastic polymer, wherein the core comprise one of a biodegradable metal, metal alloy and glass-metal.

Bone anchors according to exemplary embodiments of the present invention allow the implant to fully resorb leaving no trace in the body and eliminating the need for a second procedure to remove them while reducing the risk of migration of the implant. The bone anchors used in accord with this invention may be monocortical and do not interfere with imaging.

A bone anchor according to one exemplary embodiment of the present invention includes a core comprising magnesium or a magnesium alloy. In a further exemplary embodiment, the anchor may include a spark anodization treated surface.

A bone anchor according to another exemplary embodiment includes a core comprising an iron alloy. The iron alloy may be formed by passivation in chromate solution, in borate buffer solution or in nitric acid. The iron alloy may be any suitable iron alloy such as, Fe35Mn.

A bone anchor according to a further exemplary embodiment has a core comprising an amorphous glass-metal, preferably a bulk metal glass.

In a further exemplary embodiment of the bone anchor, the bulk metal glass may be of the MgCaZn type such as, for example, $Mg_{63}Zn_{32}Ca_5$ and $Mg_{60}Zn_{35}Ca_5$, $Mg_{32}Zn_5Ca$ or $Mg_{35}Zn_5Ca$. These materials may be degraded with the formation of less hydrogen gas when contacted with water and a higher mechanical strength may be achieved.

A bone anchor according to a yet further exemplary embodiment includes a core comprising a non-bulk metal glass such as, for example, biodegradable magnesium alloys including $Mg_6ZnZr$, $Mg_3AlZn$, $MgAl_9Zn$, $Mg_3Al_{0.4}Mn$, $Mg_5Al_{0.2}Zn$, MgYRe (Re=Rare Earth), $Mg_4Zn_{1.7}Ce_{0.6}Zr$. A typical member is known commercially as WE43.

In a still further exemplary embodiment, the non-bulk metal glass may be treated at its surface by hard anodization according to ASTM B893, spark anodization, plasma electrolyte oxidation, micro-arc oxidation (MAO) or anodization at 100V.

In another exemplary embodiment of the bone anchor, the thermoplastic polymer is biodegradable and may belong to the polylactide or caprolactone family including all the copolymers for these families.

In another exemplary embodiment of the bone anchor, the core may be hollow such that the metallic material to be degraded may be minimized.

In again another exemplary embodiment of the bone anchor, the distal tip of the core may extend distally past a distal end of the sleeve. The distal tip of the core may be pointed so that the pointed tip can break the cortex and penetrate the bone.

In yet another exemplary embodiment of the bone anchor, the sleeve may include metallic or organic dye particles for diffracting light.

In a further exemplary embodiment, the bone anchor may additionally comprise a suture attached to the bone anchor.

In again a further exemplary embodiment of the bone anchor, the inner core may include a through bore extending transversely therethrough to allow a suture to be inserted therethrough.

In another exemplary embodiment of the bone anchor, the sleeve comprises a through opening extending transversely therethrough such that the through opening aligns with and is in communication with the through bore of the inner core.

In yet another exemplary embodiment, the bone anchor may additionally comprise an end cap attachable to the proximal end of the inner core and including a through hole extending transversely therethrough to allow a suture to be passed therethrough.

In still another exemplary embodiment of the bone anchor, the inner core comprises a hook at the proximal end of the inner core to attach a suture to the bone anchor.

According to a further aspect of the invention, the present invention relates to a method for inserting the bone anchor into a bone. The method comprising the following steps: a) inserting the bone anchor into bone by pressing the distal tip of the core thereagainst; and b) heating the sleeve by applying electromagnetic radiation through the sleeve, thereby softening and/or melting the thermoplastic polymer such that the sleeve expands into the surrounding bone tissue.

BRIEF DESCRIPTION OF THE DRAWINGS

Several embodiments of the invention will be described in the following by way of example and with reference to the accompanying drawings in which.

DETAILED DESCRIPTION

Figure 1:
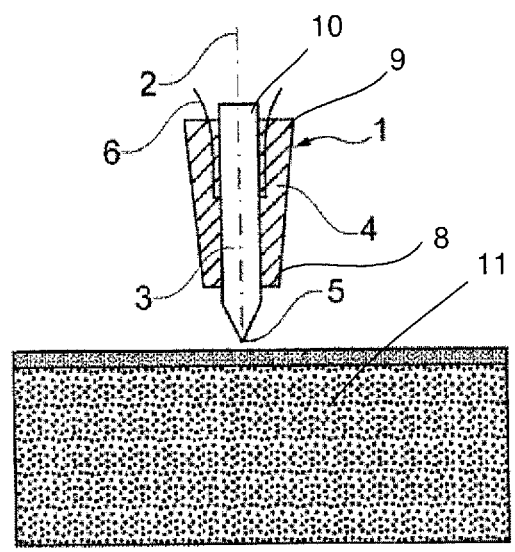
FIG. 1 illustrates a schematic longitudinal section through a bone anchor according to a first exemplary embodiment of the present invention, before insertion into bone.

The present invention may be further understood with reference to the following description and the appended drawings, wherein like elements are referred to with the same reference numerals. The present invention relates to the treatment of several bone and soft tissue injuries and, in particular, relates to a device that may be inserted and fixed within a bone. Exemplary embodiments of the present invention describe a fixation device, such as a bone anchor, including a sleeve that may be energy-activated to partially expand into surrounding bone tissue to fix the bone anchor therein. It should be noted that the terms "proximal" and "distal" as used herein, are intended to refer to a direction toward (proximal) and away from (distal) a surgeon or other user of the device.

FIGS. 1 to 4 illustrate an embodiment of a bone anchor 1 comprising an inner core 3 extending along a longitudinal axis 2 and a sleeve 4 extending about the core 3. Additionally, the bone anchor 1 further comprises a suture 6 attached to the inner core 3 and/or the sleeve 4. The suture 6 may be used to reattach soft tissue to the bone in a simple manner. The core 3 extends from a distal end 5 to a proximal end 10 and may be formed of a biodegradable metal or metal alloy, e.g. magnesium or a magnesium alloy. In a preferred embodiment, a cross-section of the core 3 is substantially circular. For example, the inner core 3 may be a solid cylinder or, alternatively, a tube to minimize an amount of metallic material to be degraded. The distal end 5 may include a sharp and/or tapered tip such that the bone anchor 1 may be inserted into a bone 11 without having to pre-drill the bone 11. The sharp and/or tapered tip 5 may break the cortex of the bone 11 when pressed thereagainst such that the bone anchor 1 may be inserted therein.

The sleeve 4 surrounds a perimeter of the core 3 and extends from a distal end 8 to a proximal end 9. The distal end 5 of the core 3 extends distally beyond the distal end 8 of the sleeve 4, however, so that the tapered distal tip of the core 3 may facilitate insertion of the bone anchor 1 into the bone 11. In addition, the proximal end 10 of the core 3 may also extend proximally past the proximal end 9 of the sleeve 4. Thus, the sleeve 4 may extend about the core 3, along only a portion of a length thereof. Further, the sleeve 4 may taper substantially conically from the proximal end 9 towards the distal end 8. The sleeve 4 may be formed as a coating on the inner core 3 or may be fixed to the inner core 3 in any known manner such as, for example, by a press fit.

The sleeve 4 may, for example, be comprised of a thermoplastic polymer, which may be chosen from the following groups: poly-alpha-hydroxyester, polyorthoester, polyanhydride, polyphosphazines, poly(propylenefumarate), polyesteramide, polyethylenefumarate, polylactide, polyglycolide, polycaprolacton, trimethylenecarbonate, polydioxanone, polyhydroxybutyrate, as well their copolymers and admixtures.

Further, the sleeve 4 may additionally comprise materials preferably chosen from the following groups: metals, carbon, ceramics, PEEK, non-thermoplastic polymers that are preferably chosen from the group of polymethylmethacrylate and/or inorganic materials such as potassium phosphate, calcium sulphate or bone cement. The sleeve 4 may also comprise the following chromophores and pigments: chlorophyll, carbon black, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, D&C yellow No. 10. In one exemplary embodiment, the sleeve 4 may comprise fluorescent chromophores which, under certain circumstances, do not absorb light but radiate off light that is absorbed from the surroundings, the polymer or any additionally introduced chromophore.

Figure 3:
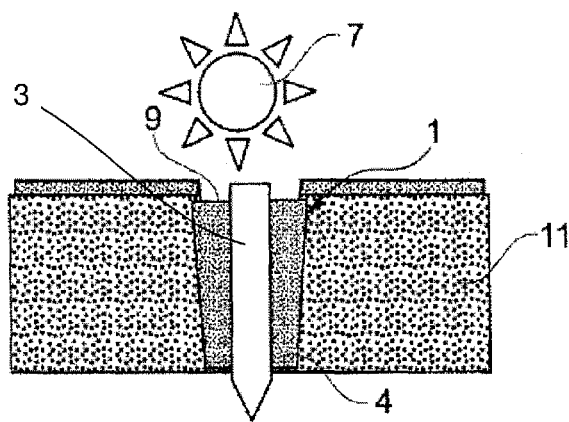
FIG. 3 illustrates the activation of the inserted bone anchor of FIG. 2 by irradiation of laser light through its sleeve.
Figure 4:
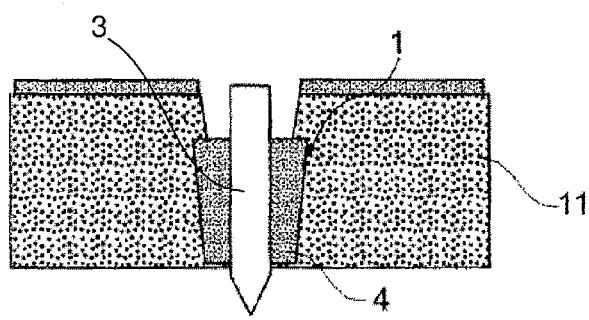
FIG. 4 illustrates the softened, partly melted sleeve material of FIG. 3, which has penetrated into the surrounding bone structure.

These additional materials may be provided in the form of metallic or organic dye particles distributed throughout the sleeve 4 or within a portion of the sleeve 4 through a partial volume of the sleeve 4 only. The metallic or organic dye particles may act to diffract light when the sleeve 4 is heated by a radiation device 7, e.g. a laser, as shown in FIG. 3. Additionally, the inner core 3 may act as a reflector for the electromagnetic radiation applied to the bone anchor 1 during its fixation in the bone 11. When the sleeve 4 is heated by applying electromagnetic radiation through the sleeve 4, the thermoplastic polymer is softened and partially melted so that the sleeve 4 expands into the surrounding bone tissue. After the electromagnetic radiation is turned off the material of the sleeve 4 cools off and solidifies so that the sleeve 4 is fixed in a cavity of the bone 11, as shown in FIG. 4.

Figure 2:
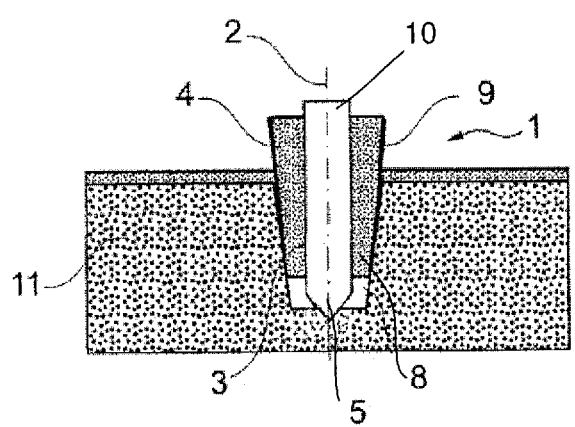
FIG. 2 illustrates the bone anchor of FIG. 1 after insertion/impaction into bone via its tip.

According to an exemplary embodiment of the present invention, the bone anchor 1 may be inserted into the bone 11 to fix a fracture and/or fix an implant, such as a bone plate, to the fractured bone 11. The bone anchor 1 may be inserted into the bone 11, as shown in FIG. 2, by pressing the tapered distal end 5 into the bone 11. Once the bone anchor 1 has been inserted into the bone 11, as desired, the sleeve 4 is activated by an energy source 7. Suitable energy sources include a radiation device, a laser, a heat source, an electromagnetic field, a light source, or an ultrasound device. Other energy sources are of course possible as would be understood by the person skilled in the art. As shown in FIG. 3, the energy source is a heat source which heats the sleeve 4 such that the sleeve 4 partially melts, expanding into the surrounding bone tissue, as shown in FIG. 4. The melted sleeve 4 solidifies as it cools, anchoring the bone anchor 1 in the bone 11.

Figure 5:
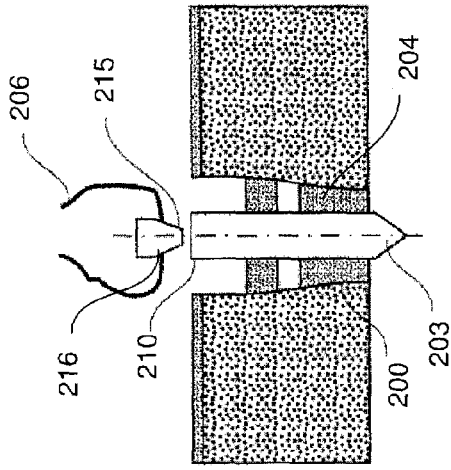
FIG. 5 illustrates a schematic longitudinal section through a bone anchor according to a further exemplary embodiment of the present invention.

FIG. 5 illustrates another embodiment of a bone anchor 100 which may be substantially similar to the bone anchor 1, as described above in regard to FIGS. 1 to 4. The bone anchor 100 similarly comprises an inner core 103 surrounded by a sleeve 104, which may be heat activated. The inner core 103, however, comprises a through bore 113 extending transversely therethrough. In addition, the sleeve 104 includes a corresponding through opening 114 which aligns with the through bore 113 of the inner core 103. The through bore 113 may be located in a middle portion of the core 103 along a length of the inner core 103 while the through opening 114 may be located toward a proximal end 109 of the sleeve 104. A suture 106 may pass through the through bore 113 in the inner core 103 and said the corresponding through opening 114 in the sleeve 104 such that the suture 106 is attached to both the inner core 103 and the sleeve 104.

Figure 6:
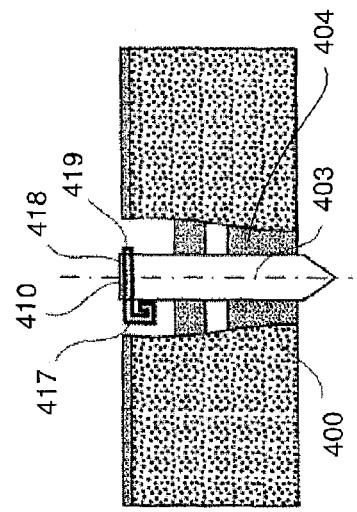
FIG. 6 illustrates a schematic longitudinal section through a bone anchor according to another exemplary embodiment of the present invention.

FIG. 6 illustrates a further embodiment of a bone anchor 200, which may be substantially similar to the bone anchor 1, as described above. The bone anchor 200 similarly comprises an inner core 203 and a sleeve 204 extending about the inner core 203. The bone anchor 200, however, additionally comprises an end cap 215 which is adapted and configured to be coupled to a proximal end 210 of the inner core 203. The end cap 215 may include, for example, a conical joining sized and shaped to be inserted into and coupled with the proximal end 210 of the core 203. The end cap 215 may include a through hole 216 extending transversely therethrough (e.g., substantially perpendicular to a longitudinal axis 202 of the bone anchor 200) allowing a suture 206 to pass therethrough such that the suture 206 may be fixed within the proximal end 210.

Figure 7:
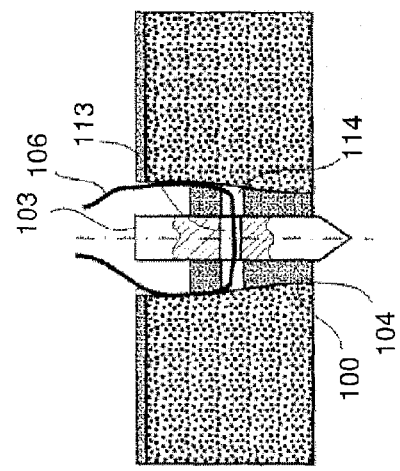
FIG. 7 illustrates a schematic longitudinal section through a bone anchor according to a further exemplary embodiment of the present invention.

FIG. 7 illustrates another embodiment of a bone anchor 300, which may be substantially similar to the bone anchor 1, as described above, comprising an inner core 303 surrounded by a sleeve 304 extending about a periphery thereof. The inner core 303, however, further comprises a through bore 313 extending transversely therethrough. The through bore 313 extends through the core 303, proximate a proximal end 310 of the inner core 303 and proximally of a proximal end 309 of the sleeve 304. Thus, the suture 306 may pass through the through bore 313 of the inner core 303 without passing through any portion of the sleeve 304.

Figure 8:
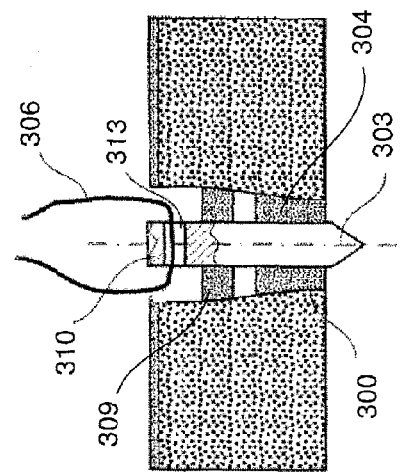
FIG. 8 illustrates a schematic longitudinal section through a bone anchor according to yet another exemplary embodiment of the present invention.

FIG. 8 illustrates yet a further embodiment of a bone anchor 400, which may be substantially similar to the bone anchor 1, as described above, comprising an inner core 403 and a sleeve 404 extending about the core 403. The inner core 403, however, further comprises a hook 417 at a proximal end 410 thereof. The hook 417 includes a ring 419 sized and shaped to receive the proximal end 410 of the inner core 403 to attach the hook 417 thereto. The ring 419 may be attached to the inner core 403 via, for example, a press fit. Alternatively, the hook 417 may include a thread 418 along an inner surface 419 of the ring 419, which engages a threaded portion of the inner core. The hook 417 facilitates attachment of a suture to the inner core 403.

The present invention has been described using an embodiment where the fixation device is a bone anchor used to suture and reattach soft tissue to bone. It will be appreciated by persons skilled in the art that other embodiments are of course possible. One such embodiment is a bone screw (not shown). The bone screw has generally the same configuration as the previously described embodiments except that the bone screw does not feature a suture. The bone screw may also include a screw head to, for example, enable the screw to act as an anchor for fixing a bone plate in position on a selected area of a bone requiring fixation.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A bone fixation system comprising:
    an energy source; and
    a bone fixation device including:
        a biodegradable inner core extending along a longitudinal axis, such that the biodegradable inner core defines a tapered distal tip that is configured to break a cortical portion of a bone when the fixation define is inserted into the bone along the longitudinal axis; and
        a sleeve defining a proximal end and a distal end opposite the proximal end, such that in an assembled configuration, the sleeve surrounds the biodegradable inner core along a portion of a length thereof such that the distal tip of the biodegradable inner core extends distally past the distal end of the sleeve, the sleeve comprising a thermoplastic polymer formed of a material which softens and expands into surrounding bone tissue when activated by the energy source,
    wherein the fixation device is configured to be inserted into the bone in the assembled configuration.

2. The bone fixation system according to claim 1, wherein the biodegradable inner core is a biodegradable metallic inner core.

3. The bone fixation system according to claim 2, wherein the biodegradable metallic inner core comprises one of magnesium, a magnesium alloy, and an iron alloy.

4. The bone fixation system according to claim 2, wherein the biodegradable metallic inner core comprises a bulk metal glass.

5. The bone fixation system according to claim 4, wherein the bulk metal glass is of a MgCaZn type.

6. The bone fixation system according to claim 4, wherein the bulk metal glass is one of $Mg_{53}Zn_{32}Ca_5$, $Mg_{60}Zn_{35}Ca_5$, $Mg_{32}Zn_5Ca$, or $Mg_{35}Zn_5Ca$.

7. The bone fixation system according to claim 1, wherein the biodegradable inner core comprises a non-bulk metal glass.

8. The bone fixation system according to claim 7, wherein the non-bulk metal glass is one of $Mg_5ZnZr$, $Mg_3AlZn$, $MgAl_9Zn$, $Mg_3Al_{0.4}Mn$, $Mg_6Al_{0.2}Zn$, MgYRe (Re=Rare Earth), $Mg_4Zn_{1.7}Ce_{0.6}Zr$.

9. The bone fixation system according to claim 7, wherein the non-bulk metal glass has a surface treated by one of hard anodization and micro-arc oxidation (MAO).

10. The bone fixation system according to claim 1, wherein the thermoplastic polymer is biodegradable.

11. The bone fixation system according to claim 1, wherein the biodegradable inner core is hollow.

12. The bone fixation system according to claim 1, wherein the sleeve comprises one of metallic and organic dye particles that diffract light.

13. The bone fixation system according to claim 1, further comprising a suture attached to the fixation device.

14. The bone fixation system according to claim 1, wherein the biodegradable inner core includes a through bore extending transversely therethrough to accommodate a suture therein.

15. The bone fixation system according to claim 1, wherein the sleeve includes a through opening extending transversely therethrough, the through opening aligned with and in communication with a through bore of the biodegradable inner core.

16. The bone fixation system according to claim 15, further comprising an end cap attachable to the proximal end of the biodegradable inner core, the end cap including a through hole extending transversely therethrough to accommodate a suture therein.

17. The bone fixation system according to claim 15, wherein the biodegradable inner core includes a hook at the proximal end thereof to attach a suture to the fixation device.

18. The bone fixation system according to claim 1, wherein the fixation device is one of a bone anchor or a bone screw.

19. The bone fixation system according to claim 1, wherein the energy source is one of a radiation device, a laser, a heat source, an electromagnetic field, a light source, or an ultrasound device.

* * * * *